US011351108B2

(12) United States Patent
Schott et al.

(10) Patent No.: US 11,351,108 B2
(45) Date of Patent: Jun. 7, 2022

(54) FINGER-MOLDABLE COMPOSITIONS CAPABLE OF FORMING A FREE-STANDING COATING

(71) Applicant: L'ORÉAL, Paris (FR)

(72) Inventors: Andrea E. Schott, New Providence, NJ (US); Alexandra Farran, Dayton, NJ (US); Anne-Laure Bernard, New York, NY (US); Erin McMullin, Ewing, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/399,485

(22) Filed: Apr. 30, 2019

(65) Prior Publication Data
US 2020/0345620 A1 Nov. 5, 2020

(51) Int. Cl.
*A61K 8/90* (2006.01)
*A61K 8/92* (2006.01)
*A61Q 1/00* (2006.01)

(52) U.S. Cl.
CPC .................. *A61K 8/90* (2013.01); *A61K 8/92* (2013.01); *A61Q 1/00* (2013.01)

(58) Field of Classification Search
CPC .............. A61K 8/90; A61K 8/92; A61Q 1/00
USPC ........................................ 424/78.03, 64, 65
See application file for complete search history.

(56) References Cited

U.S. PATENT DOCUMENTS

| 5,221,534 | A | 6/1993 | Deslauries et al. | |
| 8,124,112 | B2 * | 2/2012 | Blin | A61Q 1/06 424/401 |
| 2001/0007654 | A1 * | 7/2001 | Caes | A61K 8/90 424/70.11 |
| 2004/0234564 | A1 * | 11/2004 | Blin | A61K 8/8111 424/401 |
| 2007/0041920 | A1 | 2/2007 | Blin et al. | |
| 2007/0041929 | A1 * | 2/2007 | Torgerson | A61K 8/416 424/70.122 |
| 2008/0107697 | A1 * | 5/2008 | Blin | A61K 8/8152 424/401 |
| 2009/0196839 | A1 * | 8/2009 | Farcet | A61Q 19/007 424/59 |
| 2013/0164235 | A1 * | 6/2013 | Lebre-Lemonnier | A61Q 1/10 424/63 |
| 2015/0290109 | A1 * | 10/2015 | Simonnet | A61K 8/025 132/206 |
| 2017/0135946 | A1 * | 5/2017 | Novack | A61K 8/342 |
| 2020/0054546 | A1 * | 2/2020 | Swoboda | A61K 47/06 |

FOREIGN PATENT DOCUMENTS

EP 1 854 450 A2 * 11/2007
EP 1854450 A2 11/2007

OTHER PUBLICATIONS

International Search Report for corresponding PCT Application No. PCT/US2020/0303704 dated Aug. 5, 2020.
Written Opinion for corresponding PCT Application No. PCT/US2020/0303704 dated Aug. 5, 2020.

* cited by examiner

*Primary Examiner* — Blessing M Fubara
(74) *Attorney, Agent, or Firm* — Meagher Emanuel Laks Goldberg & Liao, LLP

(57) ABSTRACT

The present invention relates to a finger-moldable composition capable of forming a free-standing coating and suitable for application to, for example, human lips. The composition includes a thermoplastic block copolymer that includes styrenated blocks. It further includes a sufficient amount of cosmetic oil to allow a human user to mold the composition readily with the user's fingers and form a free-standing film.

9 Claims, 1 Drawing Sheet

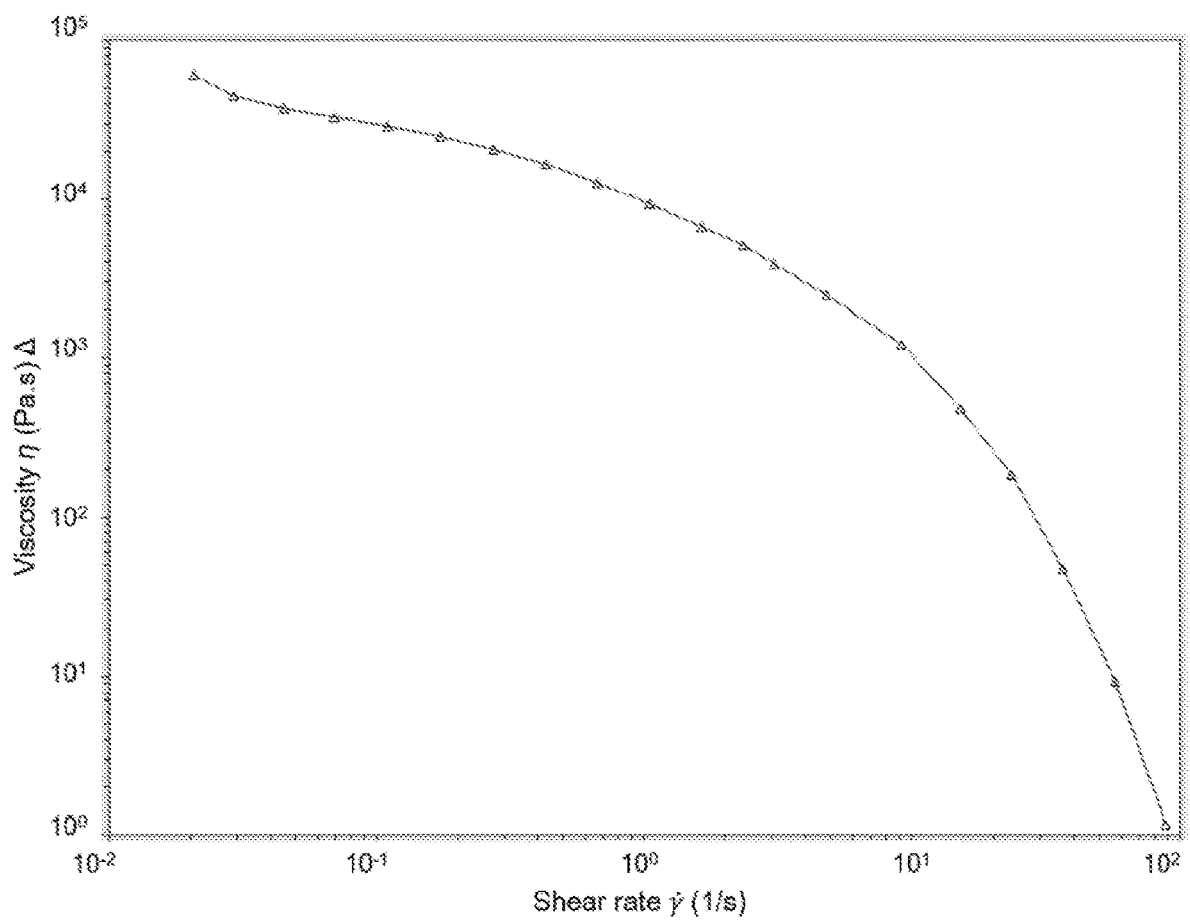

FINGER-MOLDABLE COMPOSITIONS CAPABLE OF FORMING A FREE-STANDING COATING

FIELD OF THE INVENTION

The present invention relates to compositions including block copolymers and, in particular, compositions including block copolymers capable of being molded onto the lips or other human body parts, for cosmetic and aesthetic purposes.

DISCUSSION OF THE BACKGROUND

Various compositions are known to apply to human lips for cosmetic effect. For example, lip stick and lip gloss compositions, are typically formulated to possess color, shine or gloss characteristics upon application. However, some consumers desire the appearance of increased lip volume, perhaps in addition to color, shine and other attributes.

The inventors have now identified a composition that can be molded or shaped across human lips in order to provide the appearance of volume and optionally color, gloss or other aesthetic attributes.

SUMMARY OF THE INVENTION

The present invention relates to a finger-moldable composition capable of forming a free-standing coating and suitable for application to human lips. The composition includes a thermoplastic block copolymer that includes styrenated blocks. It further includes a sufficient amount of cosmetic oil to allow a human user to mold the composition readily with the user's fingers and form a free-standing film.

According to other aspects, the present invention also relates to methods of treating, caring for and/or making up lips by applying compositions of the present invention to lips in an amount sufficient to treat, care for and/or make up lips.

According to other aspects, the present invention also relates to methods of enhancing the appearance of lips by applying compositions of the present invention to lips in an amount sufficient to enhance the appearance of lips.

According to other aspects, the present invention also relates to methods of reshaping or recountouring areas of the face or body by applying compositions of the present invention thereto.

It is to be understood that both the foregoing general description and the following detailed description are exemplary and explanatory only, and are not restrictive of the invention.

BRIEF DESCRIPTION OF FIGURES

FIG. 1 is a rheological curve showing the viscosity as a function of shear rate for a composition consistent with embodiments of the invention.

DETAILED DESCRIPTION OF THE INVENTION

As used herein, the expression "at least one" means one or more and thus includes individual components as well as mixtures/combinations.

As used herein, the expression "at least one" means one or more and thus includes individual components as well as mixtures/combinations. All concentrations/percentages listed are by weight unless otherwise noted.

Numerical ranges are inclusive of endpoints and meant to include all combinations and sub-combinations. For example, from about 5%, 10% or 15% to about 20%, 50% or 60% means about 5% to about 20%, about 5% to about 50%, about 5% to about 60%, about 10% to about 20%, about 10% to about 50%, about 10% to about 60%, about 15% to about 20%, about 15% to about 50%, or about 15% to about 60%.

Other than in the operating examples, or where otherwise indicated, all numbers expressing quantities of ingredients and/or reaction conditions are to be understood as being modified in all instances by the term "about," meaning within 10% of the indicated number, such as within about 5%, such as within 1% or 2% of the indicated number.

"Polymer" as used herein means a compound which is made up of at least two monomers.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 50° C.

"Anhydrous" means the compositions contain less than 1% water. Preferably, the compositions of the present invention contain less than 0.5% water, and most preferably no water.

The compositions and methods of the present invention can comprise, consist of, or consist essentially of the essential elements and limitations of the invention described herein, as well as any additional or optional ingredients, components, or limitations described herein or otherwise useful in personal care products, especially lip products.

Finger-Moldable Compositions

In accordance with the present invention, finger-moldable compositions capable of forming a free-standing coating and suitable for application to, for example, human lips are provided. Such compositions allow for the appearance of enhanced lip volume along with ease of application, customizability, and an aesthetic appearance.

The compositions of the present invention are generally in the form of a finger-moldable, putty-like material. The compositions are "finger-moldable" in that a user can manually (using one's fingers, thumbs and the like) compress, stretch and mold the composition as to spread across the lips of the user. Accordingly, although a device can be used to apply the composition to the lips, the user can do so without any of such assistance. The user may spread the composition across the upper and lower lips covering most or preferably all of the upper and lower lips of the user.

In contrast with conventional lipstick, compositions of the present invention have sufficient cohesion to form a free-standing coating. By "free-standing coating," it is meant a coating that can be physically removed (e.g., "peeled off") from the lips, such as with one's fingers, in a manner such that the coating retains its much of its mechanical integrity. Stated differently, the coating has enough cohesion so that most or all of the coating can be peeled off together at once, leaving essentially no colorant behind on the lips.

Thermoplastic Block Copolymer Comprising Styrenated Blocks

The block copolymers of the present invention are characterized by the presence of at least one "hard" segment, and at least one "soft" segment. Aside from their compositional nature, the hard and soft segments of the block copolymers of the present invention may be defined in terms of their respective glass transition temperatures, $T_g$. The hard segment may have a $T_g$ of 50° C. or more, whereas the soft segment may have a $T_g$ of 20° C. or less. The $T_g$ for the hard block can range from 50° C. to 150° C. The $T_g$ for the soft block can range from can range from −150° C. to 20° C.

Block copolymers useful in compositions of the present invention may be thermoplastic elastomers. The hard segments of the thermoplastic elastomer typically comprise vinyl monomers in varying amounts. Examples of suitable vinyl monomers include, but are not limited to, styrene as well as other optional monomers including methacrylate, acrylate, vinyl ester, vinyl ether, vinyl acetate, and the like.

The soft segments of the thermoplastic elastomer comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, poly-isoprene, polymers of hydrogenated butanes and isoprenes, and mixtures thereof.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In some embodiments, the thermoplastic elastomer of the present invention may be chosen from the class of KRATON rubbers (Kraton Corporation of Houston, Tex.) or from similar thermoplastic elastomers. KRATON rubbers are thermoplastic elastomers in which the polymer chains comprise a di-block, tri-block, multi-block or radial or star block configuration or numerous mixtures thereof. The KRATON tri-block rubbers have polystyrene (hard) segments on each end of a rubber (soft) segment, while the KRATON di-block rubbers have a polystyrene (hard) segment attached to a rubber (soft) segment. The KRATON radial or star configuration may be a four-point or other multipoint star made of rubber with a polystyrene segment attached to each end of a rubber segment. The configuration of each of the KRATON rubbers forms separate polystyrene and rubber domains.

Each molecule of KRATON rubber is said to comprise block segments of styrene monomer units and rubber monomer and/or co-monomer units. The most common structure for the KRATON triblock copolymer is the linear A-B-A block type styrene-butadiene-styrene, styrene-isoprene-styrene, styrene-ethylenepropylene-styrene, or styrene-ethylenebutylene-styrene. The KRATON di-block is preferably the AB block type such as styrene-ethylenepropylene, styrene-ethylenebutylene, styrene-butadiene, or styrene-isoprene. The KRATON rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by ExxonMobil Chemical under the tradename VECTOR.

Other thermoplastic elastomers useful in the present invention include those block copolymer elastomers comprising a styrene-butylene/ethylene-styrene copolymer (triblock), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block)).

Compositions of the present invention include at least one block copolymer, e.g, diblock, triblock, multiblock or radial block copolymers, and mixtures thereof. The at least one block copolymer comprises at least one styrene block and may further comprise at least one block comprising units chosen from butadiene, ethylene, propylene, butylene and isoprene or a mixture thereof.

Diblock copolymers that may be mentioned include but are not limited to styrene/ethylene-propylene copolymers (comprising a styrene block and a block obtained from ethylene and propylene), styrene/ethylene-butylene copolymers, styrene-ethylene/butadiene copolymers, styrene/butadiene copolymers and styrene/isoprene copolymers.

In certain notable embodiments, the block copolymer includes styrene blocks and one or more blocks selected from: butadiene blocks, isoprene blocks, and ethylene-butylene blocks. In other embodiments, the block copolymer includes (1) styrene blocks and butadiene blocks; or (2) styrene and ethylene-butadiene blocks; or (3) styrene and isoprene blocks.

Triblock copolymers that may be mentioned include but are not limited to styrene/ethylene-propylene/styrene copolymers, styrene/ethylene-butylene/styrene copolymers, styrene/ethylene-butadiene/styrene copolymers, styrene/isoprene/styrene copolymers and styrene/butadiene/styrene copolymers. For instance, triblock polymers sold under the names KRATON G1650, KRATON G1652, KRATON D1101, KRATON D1102 and KRATON, commercially available from the company Kraton Polymers.

For instance, a mixture of a diblock copolymer and of a triblock copolymer may be used as block copolymer. According to at least one embodiment, the diblock copolymer and the triblock copolymer may be chosen from block copolymers comprising at least one styrene block and at least one block comprising units chosen from butadiene, ethylene, propylene, butylene and isoprene. In one embodiment, the block copolymer has from about 50% to about 90% triblock and from about 10% to about 50% diblock.

Examples of suitable block copolymers include Kraton G series such as Kraton G1701 (INCI name of Hydrogenated Styrene/Isoprene Copolymer) and KRATON G1657 (HYDROGENATED STYRENE/BUTADIENE COPOLYMER). KRATON G1657 (styrene-ethylene/butylene-styrene triblock and 30% styrene-ethylene-butylene diblock); INCI: HYDROGENATED STYRENE/BUTADIENE COPOLYMER; a mixture of 70% styrene-ethylene-butylene triblock) is particularly notable.

It is preferred that the styrene content of the block copolymer be less than 30% by weight, preferably less than 25% by weight, and more preferably less than 20% by weight, and more preferably from about 5% to about 15%, based on the weight of the block copolymer. This is because of the tendency of block copolymers having a styrene content of greater than 30% by weight to harden/gel in conventional carrier systems.

The inventors have found that the thermoplastic block copolymer comprising styrenated blocks may desirably be present in the cosmetic composition in an amount ranging from, for example, about 16% to about 40% by weight; such as from about 20% to about 29% by weight, such as from about 20% to about 25%, based on the weight of the composition.

In certain embodiments, the thermoplastic block copolymer comprising styrenated blocks is dominant polymer in the composition. For example, the thermoplastic block copolymer comprising styrenated blocks may represent from about 50% by weight to about 100% by weight of all polymers in the composition. In other embodiments, the thermoplastic block copolymer comprising styrenated blocks may represent from about 80% by weight to about 100% by weight of all polymers in the composition.

Cosmetic Oil

The cosmetic oil is present in a sufficient amount of to allow a human user to mold the composition readily with the user's fingers and form a free-standing film.

As used herein, by "cosmetic oils," it is meant compounds suitable for cosmetic use and having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. While in certain embodiments, the oil may include fatty acids or fatty alcohols, in certain other embodiments, the oil is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy) sulfonyl moieties. In certain embodiments, the oil does not include hydroxyl moieties.

The cosmetic oil is a solvent for the thermoplastic block copolymer and therefore is capable of dissolving the thermoplastic block copolymer when mixed in proportions described herein.

Suitable silicone oils include dimethicone, cyclopentasiloxane and volatile silicones. The silicone oil may be a volatile silicone oil such as a linear or cyclic silicone oils having a viscosity at room temperature less than or equal to 6 cSt and having from 2 to 7 silicon atoms; these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures.

According to certain embodiments of the invention the cosmetic oil is selected from a hydrocarbon oil, an ester, a fatty alcohol, a fatty acids and combinations thereof. In certain other particularly notable embodiments the cosmetic oil is selected from a hydrocarbon oils, and esters. By "hydrocarbon," it is meant a material whose molecules contain only hydrogen and carbon.

Suitable hydrocarbon oils include alkanes having a carbon chain of at least eight carbons. Notable hydrocarbon oils include isododecane, isohxadecane, and isoparrafins. Suitable examples of esters include vegetable oils (glyceryl esters of fatty acids, monoglycerides, diglycerides, triglycerides) and (fatty) esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, pentaerythritol tetraoctanoate and mineral oil.

According to certain embodiments, the cosmetic oil is oligomeric or polymeric, such as an oligomeric or polymeric hydrocarbon. Suitable examples of oligomeric or polymeric hydrocarbons include polyisobutene and hydrogenated polyisobutene, such as those commercially available from Ineos and NOF Corporation.

According to certain embodiments of the invention, the cosmetic oil has a molecular weight from about 100 daltons to about 500 daltons, such as from about 150 daltons to about 250 daltons.

According to certain embodiments, the cosmetic oil is present in a concentration by weight from about 60%-85% by weight, such as from about 70% to about 80% by weight.

Additional Ingredients

According to preferred embodiments, the composition may include particulates, waxes, silicones, additional polymers, and/or colorants. The total concentration by weight of the additional ingredients may range from 0% to about 20%, such as from 0% to about 10%.

According to preferred embodiments of the present invention, compositions further comprising at least one colorant (coloring agent) is provided.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, β-carotene, soybean oil, Sudan Brown, DC Yellow 11, DC Violet 2, DC Orange 5, annatto, and quinoline yellow.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum. In certain embodiments, the colorant is present in an amount sufficient for an observer to identify the composition as having a "red" color, e.g. red, reddish-brown, pink, or the like.

If present, it is preferred that the amount of coloring agent present in the composition is less than 20%, such as less than 10%, preferably 5% or less by weight of the total weight of the composition.

Wax

According to certain embodiments of the invention, compositions may include waxes. By waxes it is meant lipophilic fatty compounds that are solid at room temperature (about 25° C.) and atmospheric pressure (760 mm Hg, i.e., 105 Pa), which undergo a reversible solid/liquid change of state and which has a melting point of greater than 30° C., and in some embodiments, greater than about 55° C. up to about 120° C. or even as high as about 200° C. In certain other embodiments, the compositions are substantially free of or completely free of waxes. If present, the amount of waxes present in the composition is less than 20%, such as less than 10%, preferably 5% or less by weight of the total weight of the composition, including all ranges and subranges therebetween such as, for example, 1% to 10%.

According to certain embodiments of the invention, compositions may include particulates such as inorganic particulates. "Inorganic particulate" means any finely divided material that is predominantly inorganic (including inorganic particulates having an organic or silicon-based coating), including titanium dioxide, talc, mica, silica, silica silylates, perlite, kaolin, as well as bismuth oxychloride, zinc oxide, among others. The inorganic pigment may be coated or uncoated.

If present, the amount of particulate present in the composition is less than 20%, such as less than 10%, preferably 5% or less by weight of the total weight of the composition, including all ranges and subranges therebetween such as, for example, 1% to 10%.

According to preferred embodiments, the composition includes additional polymers such as at least one film forming such as acrylic polymers, silicone resins, silicone acrylate copolymers, vinyl pyrrolidone (VP) containing homopolymers and copolymers, polyurethanes, polyolefins and mixtures thereof.

According to certain embodiments of the invention, the composition consists essentially of a finger-moldable composition capable of forming a free-standing coating and suitable for application to human lips, including a thermoplastic block copolymer comprising styrenated blocks; a sufficient amount of cosmetic oil to allow a human user to mold the composition readily with the user's fingers and form a free-standing film; and colorant. According to other embodiments of the invention, a finger-moldable composition that consists essentially of 16%-40% by weight of a thermoplastic block copolymer comprising styrenated blocks; 60%-85% by weight of cosmetic oils; and colorant.

The basic and novel property of the system associated with "consisting essentially of" is the ability to be molded by the fingers into a free-standing film. Accordingly, this claim element directed to the composition "consisting essentially of" the identified ingredients excludes ingredients which have a material effect on the system's basic and novel property (ability to be molded by the fingers into a free-standing film).

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

According to certain embodiments the compositions of the present invention may have a viscosity from about 200 Pas, 500 Pas or 2000 Pas to about 3000 Pas, 5000 Pas or 30,000 Pas, including all combinations of such ranges, when measured at a shear rate of 0.2 $s^{-1}$, using for example, the Discovery HR-3 magnetic bearing rheometer, available from TA Instruments of New Castle, Del. According to certain other embodiments the compositions of the present invention may have a viscosity from about 5 Pas or 10 Pas to about 50 Pas, 100 Pas or 500 Pas, when measured at a shear rate of 40 $s^{-1}$. All above cited viscosities are measured at 25° C.

Compositions of the present invention can be applied to the human body. According to certain embodiments, the compositions can be applied to the lips in order to give the appearance of increased lip volume and/or to provide treating, caring or conditioning of the lips. For example, the composition may be molded and or stretched as to spread across the lips of the user. The molding process generally reduces the composition to a thin layer that adheres to and coats the lips. This may be accomplished with the assistance of a device or the user can do so only with the user's hands. The user may spread the composition across the upper and lower lips covering most or preferably all of the upper and lower lips of the user. The composition will generally stay-in place and can give the appearance of the user's natural lips while also providing the appearance of increased volume. The inclusion of colorant in the composition can give the appearance of the user wearing conventional lipstick.

According to other embodiments, the composition can be be applied to other areas of the face of body for use as a prosthetic. Accordingly, the appearance of the face (e.g, cheeks and the like) or the body can be adapted or reshaped or recountoured to alter the appearance, to conceal injury, or to enhance certain features of the face or body.

The present invention also relates to methods of enhancing the appearance of lips by applying compositions of the present invention to lips in an amount sufficient to enhance the appearance of lips.

Compositions of the present invention may be made by any of various methods, such as by heating the oil to, for example, about 90° C. and mixing under high shear while slowly adding the thermoplastic styrenated block copolymer. Once the mixture is oil/block copolymer homogeneous, other optional ingredients may be added, such as one at a time.

Example 1—Exemplary Compositions

The following composition are exemplary compositions of the present invention which were prepared by the above method. Concentrations by weight of ingredients are shown in Table 1, below:

TABLE 1

| Ingredient | Inventive Example 1 | Inventive Example 2 | Inventive Example 3 | Inventive Example 4 |
| --- | --- | --- | --- | --- |
| KRATON G1657 | 25% | 24% | 25% | 25% |
| Isohexadecane | 74.9% | 37.5% | 0% | 0% |
| Isododecane | | 37.5% | 75% | |
| Hydrogenated polyisobutene | 0% | 0% | 0% | 75% |
| Colorant (lake pigment) | 0.1% | 1% | 0% | 0% |

Example 2—Rheology

The composition of Example 1 was prepared as above. Using the Discovery HR-3 magnetic bearing rheometer, available from TA Instruments of New Castle, Del. the viscosity as a function of shear rate was determined by examining viscosity as a function of shear rate from 0.1 (1/s) to 100 (1/s). The readings were taken at 25° C. The results are shown in FIG. 1.

What is claimed is:

1. A finger-moldable lip composition capable of forming a free-standing film and suitable for application to human lips, consisting of:
   16%-40% by weight of a thermoplastic block copolymer comprising styrenated blocks, the thermoplastic block copolymer having at least one hard segment and at least one soft segment;
   60%-85% by weight of cosmetic oils; and
   one or more colorants.

2. The finger-moldable lip composition according to claim 1,
   wherein the thermoplastic block copolymer comprising styrenated blocks is a styrene/butadiene copolymer, a styrene/isoprene copolymer, a styrene-butylene/ethylene-styrene copolymer, a styrene/ethylene-butylene copolymer, a styrene-ethylene/butadiene copolymer, an ethylene/propylene-styrene copolymer, a styrene/ethylene-propylene/styrene copolymer, a styrene/ethylene-butylene/styrene copolymer, a styrene/ethylene-butadiene/styrene copolymer, a styrene/isoprene/styrene copolymer, a styrene/butadiene/styrene copolymer, or a combination thereof, and
   wherein the cosmetic oil has a molecular weight from about 150 daltons to about 250 daltons.

3. The finger-moldable lip composition according to claim 1, wherein the thermoplastic block copolymer comprises styrene blocks and one or more blocks selected from butadiene blocks, isoprene blocks, and ethylene-butadiene blocks.

4. The finger-moldable lip composition according to claim 1, wherein the thermoplastic block copolymer comprising styrenated blocks is selected from a hydrogenated styrene/butadiene copolymer and a hydrogenated styrene/isoprene copolymer.

5. The finger-moldable lip composition according to claim 1, comprising 20%-29% by weight of the thermoplastic block copolymer comprising styrenated blocks.

6. The finger-moldable lip composition according to claim 1, wherein the cosmetic oil is selected from a hydrocarbon oil, an ester, a fatty alcohol, a fatty acid, a oligomeric or polymeric hydrocarbon, and combinations thereof.

7. The finger-moldable lip composition according to claim 1, wherein the cosmetic oil is a hydrocarbon oil.

8. The finger-moldable lip composition according to claim 7, wherein the hydrocarbon oil has a molecular weight from about 150 daltons to about 250 daltons.

9. The finger-moldable lip composition according to claim 7, wherein the cosmetic oil is isohexadecane, isododecane, isoparrafin, or a combination thereof.

\* \* \* \* \*